(12) United States Patent
Xing et al.

(10) Patent No.: US 9,399,629 B2
(45) Date of Patent: Jul. 26, 2016

(54) PROCESS FOR THE MANUFACTURE OF 3-OXO-TETRAHYDROFURAN

(71) Applicants: Lidong Xing, Shanghai (CN); Weitong Dong, Shanghai (CN); Jun Lu, Shanghai (CN); Ulrich Scholz, Bad Kreuznach (DE); Jun Yan, Shanghai (CN); Jinsong Yang, Ingelheim am Rhein (DE)

(72) Inventors: Lidong Xing, Shanghai (CN); Weitong Dong, Shanghai (CN); Jun Lu, Shanghai (CN); Ulrich Scholz, Bad Kreuznach (DE); Jun Yan, Shanghai (CN); Jinsong Yang, Ingelheim am Rhein (DE)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 0 days.

(21) Appl. No.: 14/203,666

(22) Filed: Mar. 11, 2014

(65) Prior Publication Data

US 2014/0275579 A1 Sep. 18, 2014

(30) Foreign Application Priority Data

Mar. 12, 2013 (WO) ................ PCT/CN2013/072429

(51) Int. Cl.
*C07D 307/32* (2006.01)
*C07D 307/20* (2006.01)
*C07D 315/00* (2006.01)

(52) U.S. Cl.
CPC ............ *C07D 307/32* (2013.01); *C07D 307/20* (2013.01)

(58) Field of Classification Search
CPC ... C07D 307/32; C07D 315/00; C07D 307/20

USPC .......................................... 549/475
See application file for complete search history.

(56) References Cited

U.S. PATENT DOCUMENTS 5,821,374 A 10/1998 Jenny et al.
2009/0286828 A1 11/2009 Bozzoli et al.

FOREIGN PATENT DOCUMENTS

WO WO 2007090840 A1 * 8/2007

OTHER PUBLICATIONS

Wynberg, H., "3-hydroxytetrahydrofuran", Organic Syntheses 1958, 38: 37-38.*
Lichtenthaler, F.W., "Carbohydrates as Organic Raw Materials", 2010,Wiley-VCH Verlag GmbH & Co. KGaA, Weinheim, p. 1-33.*
De Luca, L. et al., "Trichloroisocyanuric/TEMPO Oxidation of Alcohols under Mild Conditions: A Close Investigation." The Journal of Organic Chemistry, 2003, vol. 68, No. 12, pp. 4999-5001.
Hiegel, G. at al., "The Oxidation of Secondary Alcohols to Ketones With Trichloroisocyanuric Acid." Synthetic Communications: An International Journal for Rapid Communication of Synthetic Organic Chemistry, 1992, vol. 22, pp. 1589-1595.
International Search Report and Written Opinion for PCT/EP2014/054711 mailed May 19, 2014.

* cited by examiner

*Primary Examiner* — Samantha Shterengarts
*Assistant Examiner* — Matt Mauro
(74) *Attorney, Agent, or Firm* — Michael P. Morris; David L. Kershner; Atabak R. Royace

(57) ABSTRACT

This invention relates to a novel method for the preparation of 3-oxo-tetrahydrofuran comprising oxidizing 3-hydroxy-tetrahydrofuran in the presence of a catalytic amount of 2,2,6,6-tetramethyl-piperidine-N-oxyl (TEMPO) with trichloroisocyanuric acid.

6 Claims, No Drawings

PROCESS FOR THE MANUFACTURE OF 3-OXO-TETRAHYDROFURAN

FIELD OF THE INVENTION

This invention relates to a novel method for the preparation of 3-oxo-tetrahydrofuran.

BACKGROUND OF THE INVENTION

3-Oxo-tetrahydrofuran (3-Oxo-THF, compound I) is an important intermediate in the manufacture of pharmaceutically active ingredients.

The known chemical syntheses of this compound offer only limited access to 3-Oxo-THF and all face severe drawbacks that do not allow for a sustainable and environmentally friendly supply with this important intermediate. Therefore, there has been need to develop a novel approach to this compound. The present invention provides a simple, inexpensive, chemoselective and environmentally friendly process for the manufacture of 3-Oxo-THF (I) that can be run under mild conditions.

Up to date, the following methods for the preparation of 3-Oxo-THF (I) have been described: 3-Oxo-THF (I) can be prepared by using transition-metal, especially Cr (VI) as an reagent (scheme 1) to oxidize of 3-hydroxy tetrahydrofuran (3-OH-THF, compound II) [*J. Org. Chem.* 1989, 54, 1249-1256].

Scheme 1. Oxidation with pyridinium chlorochromate (PCC) (variant 1)

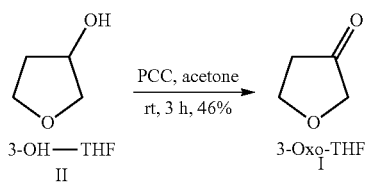

The disadvantage of this process is the toxicity and environmental hazards associated with chromium compounds. Additionally, this process delivers low yields only (up to 46%).

A modification of this synthesis is disclosed in WO 2006/067430. Therein, solvent was changed from acetone to dichloromethane (DCM) and crude yield was improved to 79%. However, all major disadvantages remain.

Scheme 2. Oxidation with PDC (variant 2 for oxidation step)

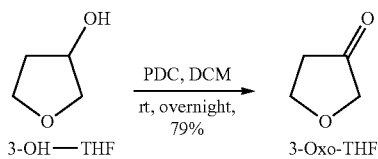

Another process for making 3-Oxo-THF is disclosed in CN 102321054A. This involves a two-step synthesis starting from but-2-yne-1,4-diol (compound III) followed by cyclization (Scheme 3). This process has the disadvantage of low conversion and high level of impurities which render it inappropriate for practical use.

Scheme 3. Process according to CN 102321054

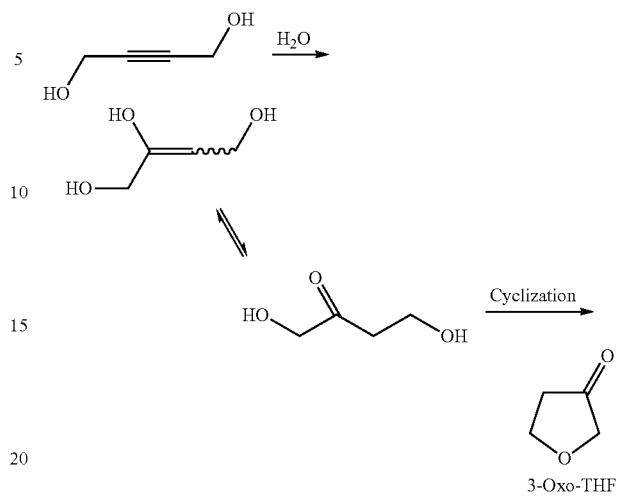

In *J. Org. Chem.* 1987, 52, 2559, oxoammonium salts like 2,2',6,6'-tetramethylpiperidine-N-oxyl or derivatives (TEMPO) were employed as oxidants in the conversion of primary and secondary alcohol function to the corresponding carbonyl function. In particular, the variant using the TEMPO-bleach combination including bromide as co-catalyst is nowadays often applied in organic syntheses [Scheme 4].

Scheme 4. TEMPO-BLEACH protocol (variant 3 for oxidation step)

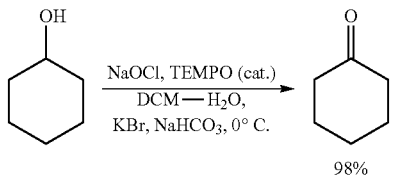

The major drawbacks of this method include (1) the use of NaClO as oxidant, (2) the need for the addition of KBr and buffering of pH at 8.6 with NaHCO$_3$ and (3) the necessity to use mixtures of chlorinated organic solvent with water. These conditions prove to be difficult for large scale applications because of the uncontrollable highly exothermic nature of the reaction.

The resulting 3-oxo-THF is unstable in the presence of excess of bleach causing the decomposition of the product. In addition, yields vary with incomplete conversion of starting material and decrease of concentration of NaClO upon the prolonged storage. Therefore, this method is not feasible for an economically competitive and robust way to allow for industrial scale production of 3-oxo-THF.

A modification of the variant 3 process is the TEMPO-TCCA protocol described in *J. Org. Chem.* 2003, 68, 4999-5001. Using trichloroisocyanuric acid (TCCA) in the presence of catalytic amount of TEMPO makes it possible to run the reaction under mild conditions. However, it is still a lab procedure. Excess use of TCCA (2 eq.) is required to complete the reaction in time. Using mixtures of solvents (water and acetone) complicates solvent recovery. Adding the oxidant TCCA after charging the TEMPO catalyst may result in an accumulation of unreacted starting materials thereby leading to a run away reaction.

Scheme 5. TEMPO—TCCA protocol (variant 4 for oxidation step)

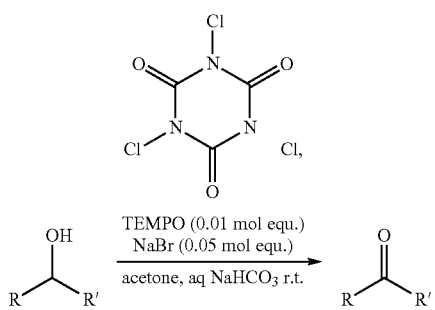

When applying this procedure to oxidize 3-OH-THF (II), complete conversion of starting material was reached after 1 h and 3-oxo-THF (I) was obtained in a yield of 69% (GC area %; comparative example 1). Lots of unidentified impurities were found by GC-MS during the reaction rendering purification difficult.

The present invention provides a method for the preparation of 3-oxo-THF that overcomes the disadvantages of these methods known in the prior art.

The process according to the present invention does not require the use of $NaHCO_3$ buffering, NaBr or other additives and delivers 3-oxo-THF with good yields and in high quality without toxic by-products and transition metal wastes.

DETAILED DESCRIPTION OF THE INVENTION

The present invention provides a novel process for preparing 3-oxo-tetrahydrofuran comprising reacting 3-hydroxy tetrahydrofuran (II)

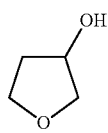

with 0.5-2 mol equivalent of trichloroisocyanuric acid

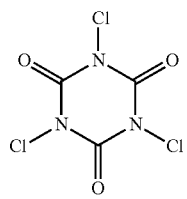 [SMILES: O=c1n(Cl)c(=O)n(Cl)c(=O)n1Cl]

in the presence of 0.001-1 mol equivalent 2,2,6,6-tetramethylpiperidine-N-oxyl (TEMPO) in a solvent selected from the group consisting of dichloromethane, ethyl acetate, isopropyl acetate, acetone, acetonitrile and toluene;
at a temperature from −20° C. to 40° C.

In a second embodiment, the process according to the first embodiment above further comprises neutralization of the reaction mixture with an inorganic base such as $NaHCO_3$, $Na_2CO_3$, or NaOH; preferably $NaHCO_3$.

In another embodiment, the process according to any one of the embodiments above further comprises quenching the reaction mixture with a reducing agent, preferably sodium sulfite.

In another embodiment, the process according to any one of the embodiments above is conducted at a temperature of −10° C. to 25° C.

In another embodiment, the process according to any one of the embodiments above is conducted in the absence of $HCO_3^-$ buffering and a bromide or other additives.

In another embodiment, in the process according to any one of the embodiments above the amount of trichloroisocyanuric acid is 1.0 to 2.0 mole equivalent, preferably 1.0 to 1.05 mol equivalent.

In another embodiment, in the process according to any one of the embodiments above the amount of TEMPO is 0.01 to 0.02 mol equivalent.

In another embodiment, in the process according to any one of the embodiments above, a solution of TEMPO in dichloromethane or ethylacetate is slowly added to the solution of 3-OH-THF and TCCA to allow for safer process and better quality control.

Another aspect of the present invention is a two-step process for preparing 3-Oxo-THF comprising the following steps
(a) conversion of butane-1,2,4 triol (III) in the presence of an acid to 3-hydroxy tetrahydrofuran (II), and
(b) conversion of 3-hydroxy terahydrofuran according to any of the embodiments of the oxidation process above.

The cyclization in step a) is conducted in the presence of a strong acid, such as p-toluenesulfonic acid (PTSA) at a temperature of 150° C. to 200° C., preferably 160° C. to 180° C.

Scheme 6. An embodiment of the two-steps synthesis of 3-oxo-THF (see also Examples 1 and 2 of the Experimental Section)

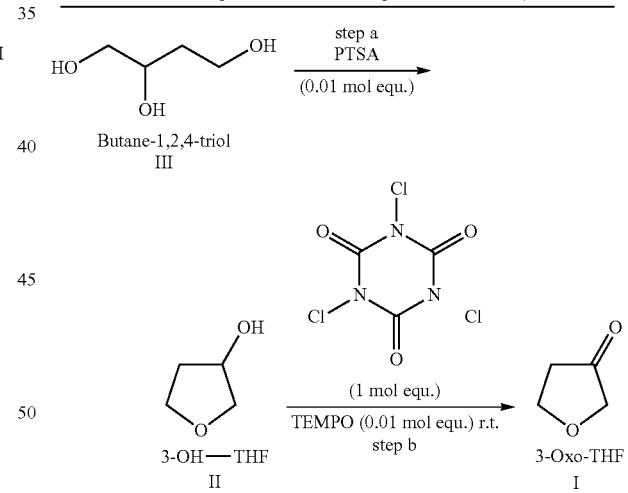

Experimental Section

Example 1

Preparation of 3-OH-tetrahydrofuran (II)

To a 500 mL flask, 1,2,4-trihydroxybutane (III, 159 g, 1.5 mol, 1 eq.) and p-toluenesulfonic acid monohydrate (1.5 g, 8.72 mmol, 0.006 eq.) were added. The solution was heated to 160-180° C. Reaction was monitored by GC. The resulting mixture was purified by fractional distillation to give 3-OH-tetrahydrofuran as colorless oil (120.5 g 91.3% yield).

Example 2

Preparation of 3-Oxo-tetrahydrofuran (3-OH-THF) in DCM

To a 1 L jacket reactor (reactor A), 3-tetrahydrofuran (3-OH-THF, 60.6 g, 0.68 mol, 1 eq.) was charged, followed by DCM (500 mL). The solution was cooled to −5° C. To which TCCA (159.6 g, 0.68 mol, 1 eq.) was added in one portion. The resulting slurry was stirred for 10 min. TEMPO (1.08 g, 0.0069 mol, 0.01 eq.) DCM solution (120 mL) was added dropwise while controlling the temperature around −5° C. to 0° C. The resulting mixture was allowed to warm to room temperature and monitored by GC-MS until the 3-OH-THF was less than 1%.

The mixture was filtered and washed with DCM (60 mL*3), followed by washing with saturated aqueous NaHCO₃. The aqueous phase was extracted with DCM (60 mL*2). The combined organic phase was concentrated in normal pressure and then distilled under vacuum to give product as pale yellow oil (55.4 g, 93.6%) with 95% HPLC purity.

Example 3

Preparation of 3-Oxo-tetrahydrofuran (3-OH-THF) in acetone

To a 250 mL flask, 3-tetrahydrofuran (3-OH-THF, 6.06 g, 0.068 mol, 1 eq.) was charged, followed by acetone (50 mL). The solution was cooled to −5° C. To which TCCA (16.0 g, 0.068 mol, 1 eq.) was added in one portion. The resulting mixture was stirred for 10 min. TEMPO (0.11 g, 0.00069 mol, 0.01 eq.) acetone solution (12 mL) was added dropwise while controlling the temperature around −5° C. to 0° C. The resulting mixture was allowed to warm to room temperature and monitored by GC-MS, the reaction was finished in 1 h to give 52% yield (GC area %).

Example 4

Preparation of 3-Oxo-Tetrahydrofuran (3-OH-THF) in Ethyl Acetate

To a 500 mL flask, 3-tetrahydrofuran (3-OH-THF, 30.3 g, 0.34 mol, 1 eq.) was charged, followed by ethyl acetate (250 mL). The solution was cooled to −5° C. To which TCCA (80.0 g, 0.34 mol, 1 eq.) was added in one portion. The resulting mixture was stirred for 10 min. TEMPO (0.54 g, 0.0035 mol, 0.01 eq.) ethyl acetate solution (60 mL) was added dropwise while controlling the temperature around −5° C. to 0° C. The resulting mixture was allowed to warm to room temperature and monitored by GC-MS. Reaction was finished in 1 h to give 90% yield (GC area %).

Example 5

Preparation of 3-Oxo-Tetrahydrofuran (3-OH-THF) in Isopropyl Acetate

To a 50 mL flask, 3-tetrahydrofuran (3-OH-THF, 0.44 g, 0.005 mol, 1 eq.) was charged, followed by isopropyl acetate (4.5 mL). The solution was cooled to −5° C. To which TCCA (1.16 g, 0.005 mol, 1 eq.) was added in one portion. The resulting mixture was stirred for 10 min. TEMPO (0.008 g, 0.00005 mol, 0.01 eq.) was added in drops while controlling the temperature around −5° C. to 0° C. The resulting mixture was allowed to warm to room temperature and monitored by GC-MS, Reaction was finished in 1 h to give 90% yield (GC area %).

Example 6

Preparation of 3-Oxo-Tetrahydrofuran (3-OH-THF) in Toluene

To a 50 mL flask, 3-tetrahydrofuran (3-OH-THF, 0.44 g, 0.005 mol, 1 eq.) was charged, followed by toluene (4.5 mL). The solution was cooled to −5° C. To which TCCA (1.16 g, 0.005 mol, 1 eq.) was added in one portion. The resulting mixture was stirred for 10 min. TEMPO (0.008 g, 0.00005 mol, 0.01 eq.) was added in drops while controlling the temperature around −5° C. to 0° C. The resulting mixture was allowed to warm to room temperature and monitored by GC-MS, Reaction was finished in 1 h to give 89% yield (GC area %).

Example 7

Changing the Adding Sequence (First TEMPO, then TCCA)

To a 1 L flask, 3-tetrahydrofuran (3-OH-THF, 60.6 g, 0.68 mol, 1 eq.) was charged, followed by DCM (620 mL) and TEMPO (1.08 g, 0.0069 mol, 0.01 eq.) The solution was cooled to −5° C. To which TCCA (159.6 g, 0.68 mol, 1 eq.) was added in portions controlling the temperature around −5° C. to 0° C. The resulting mixture was allowed to warm to room temperature and monitored by GC-MS, Reaction was finished in 1 h to give 95% yield (GC area %).

The invention claimed is:

1. A process for preparing 3-oxo-tetrahydrofuran comprising reacting 3-hydroxy tetrahydrofuran (II)

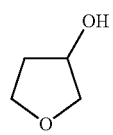

with 0.5-2 mol equivalents of trichloroisocyanuric acid

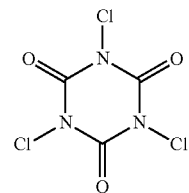 [SMILES: O=c1n(Cl)c(=O)n(Cl)c(=O)n1Cl]

in the presence of 0.001-1 mol equivalent 2,2,6,6-tetramethylpiperidine-N-oxyl (TEMPO) in a solvent selected from the group consisting of dichloromethane, ethyl acetate, isopropyl acetate and toluene; and at a temperature of −20° C. to 40° C., wherein the process is conducted in the absence of $HCO_3^-$, a bromide or other additives.

2. The process according to claim 1 wherein the reaction is conducted at a temperature of −10° C. to 25° C.

3. The process according to claim 1 wherein the amount of trichloroisocyanuric acid is 1.0 to 2.0 mol equivalent.

4. The process according to claim 1 wherein the amount of TEMPO is 0.01 to 0.02 mol equivalent.

5. The process according to claim 1 wherein in the oxidation step a solution of TEMPO in dichloromethane or ethylacetate is added to the solution of 3-hydroxy tetrahydrofuran and trichloroisocyanuric acid.

6. The process according to claim 1 wherein the trichloroisocyanuric acid is added in portions to the solution of 3-hydroxy tetrahydrofuran and TEMPO in dichloromethane or ethylacetate.

* * * * *